United States Patent [19]
Gerner et al.

[11] Patent Number: 5,607,581
[45] Date of Patent: Mar. 4, 1997

[54] DEBUBBLING AND PRIMING SYSTEM FOR CHROMOTOGRAPHY

[75] Inventors: Yuri Gerner, Mendota Heights; Carl W. Sims, St. Paul, both of Minn.

[73] Assignee: Systec, Inc., Minneapolis, Minn.

[21] Appl. No.: 551,104

[22] Filed: Oct. 31, 1995

[51] Int. Cl.⁶ ................................. B01D 15/08
[52] U.S. Cl. ............... 210/198.2; 210/188; 210/656; 96/101
[58] Field of Search ................... 210/656, 659, 210/101, 188, 198.2; 95/83; 96/101; 73/61.56

[56] References Cited

U.S. PATENT DOCUMENTS

| | | | |
|---|---|---|---|
| 3,220,246 | 11/1965 | Barnum | 73/53 |
| 3,346,486 | 10/1967 | Winter et al. | 210/31 |
| 3,465,595 | 9/1969 | Tansony | 73/421 |
| 3,640,822 | 2/1972 | Hrdina | 210/198.2 |
| 3,777,572 | 12/1973 | Hrdina | 73/422 GC |
| 3,951,855 | 4/1976 | Principe et al. | 252/408 |
| 3,954,617 | 5/1976 | Ishimatsu | 210/198.2 |
| 3,975,946 | 8/1976 | Ball | 73/61.1 C |
| 4,116,046 | 9/1978 | Stein | 210/198.2 |
| 4,444,066 | 4/1984 | Ogle | 73/863.72 |
| 4,448,684 | 5/1984 | Paradis | 210/198.2 |
| 4,454,749 | 6/1984 | Guillemin et al. | 73/23.1 |
| 4,541,452 | 9/1985 | Paradis | 210/198.2 |
| 4,954,149 | 9/1990 | Fullemann | 55/386 |
| 4,994,180 | 2/1991 | Sims | 210/198.2 |
| 5,234,587 | 8/1993 | Allington | 210/198.2 |
| 5,265,642 | 11/1993 | Buckminster | 210/198.2 |
| 5,279,647 | 1/1994 | Gatten | 96/6 |
| 5,290,340 | 3/1994 | Gatten | 95/46 |
| 5,387,395 | 2/1995 | Coassin et al. | 422/81 |
| 5,474,677 | 12/1995 | Naka | 210/656 |

*Primary Examiner*—Ernest G. Therkorn
*Attorney, Agent, or Firm*—Haugen and Nikolai PA

[57] ABSTRACT

A solvent debubbling/priming device for use in high pressure liquid chromatographic applications includes a valve adapted for releasable and sealed attachment to a bubble collecting/solvent reservoir. The valving portion of the device comprises a valve body with bores formed therein for controlled access and communication between the bubble collecting/solvent reservoir and the exterior of the valve, or atmosphere. The solvent debubbling/priming means includes a length of flexible tubing which has a flattened portion at its distal end and with the tubing being in communication with the bubble collecting/solvent reservoir. The flexible tubing along with its flattened portion provides a flow control and check valve which is chemically inert and free of potentially contaminating lubricants for effective utilization.

9 Claims, 4 Drawing Sheets

DEBUBBLING AND PRIMING SYSTEM FOR CHROMOTOGRAPHY

BACKGROUND OF THE INVENTION

The present invention relates generally to an improved debubbler/primer valve device, and more particularly to a solvent debubbler/primer means for use in connection with solvent components utilized in high pressure liquid chromatographic (HPLC) applications. The device provides a rapid, efficient and reliable valve structure for achieving removal of bubbles and ultimate pressurization of the system pump inlet to prime the pump, with this being accomplished in the absence of check valves or other system components which frequently require moving parts and lubricants. The apparatus of the present invention has found particular usefulness in applications which require extreme purity of the solvent component, free of bubbles, in high pressure liquid chromatographic (HPLC) applications by utilizing components which do not risk system contamination, and withstand long term exposure to the full range of solvents typically used in HPLC.

In the undertaking of various operations in the high pressure liquid chromatographic (hereinafter "HPLC") sequences, it is essential that the solvent (referred to as "mobile phase" by HPLC practitioners) employed be free of bubbles which may contribute cavitation and/or partial vaporization in the inlet of the system pump. A bubble may be defined as a ball of gas or air contained in a liquid or solid medium. The system pump may, in certain instances, be a positive displacement pump which, on the inlet stroke, reduces the pressure for the zone occupied by the incoming solvent. When the solvent contains bubbles inaccurate metering of solvent by the positive displacement pump does occur. Therefore, in the solvent delivery system, it is highly desirable to provide a control valve and means of capturing incoming bubbles entrained in the system, particularly from the inlet stream of solvent. The syringe provides a means to periodically remove captured air (in the vial) and apply pressure to facilitate priming of the system pump.

In the past, various apparatus and techniques have been employed for permitting and accomplishing these priming control operations, including the utilization of control valve systems having poppets and/or other check valves present for controlling solvent reservoir pressure. Such devices have been found to contribute to a source of gas or contamination, or to offer a significant restriction of flow to the system pump, and as such, have been found to be undesirable because they degrade the performance of the HPLC system. The apparatus of the present invention utilizes a length of thin-walled tubing fabricated from polytetrafluoroethylene thermoformed flat so that when exposed to pressure differentials wherein the external pressure exceeds the internal pressure, the reverse bias prevents flow. The length of polytetrafluoroethylene thermoformed tubing functions as a check valve in the overall operation, and prevents back-flow from the priming valve back to the solvent reservoir. This is achieved without the utilization of mechanical check valves which frequently require cleaning in order to ensure positive control (preventing back-flow) to the solvent reservoir. The present arrangement permits the controllable blocking of back-flow while providing a low flow resistance path from the supply solvent reservoir to the pump, yet prevent back-flow of solvent back into the solvent supply reservoir.

SUMMARY OF THE INVENTION

The solvent primer/debubbler means of the present invention includes a valve body having bores formed therein for controlled access between the main solvent reservoir and the system pump, while at the same time providing a mechanism for the temporary containment and ultimate removal of bubbles from the system. The valve body consists essentially of an inner core member and an outer sleeve member, with these members being concentrically arranged. The core and sleeve members have a plurality of bores formed therethrough which provides communication between the main solvent reservoir and the system pump, with the valve body being adapted to removably receive a gas bubble trapping reservoir. A plurality of means are disposed in cooperative relationship with the bores for controlling fluid flow from the main solvent reservoir as indicated by the specific application. A selected one of the fluid flow control means includes a length of flexible tubing which is disposed within the selected bore, and which extends into a zone communicating with the bubble collecting/solvent reservoir or alternatively, solvent receptacle/bubble trapping reservoir. The outer diameter of the flexible tubing is substantially less than the inner diameter of the bore so that the tubing is fully exposed to the pressure within the bubble collecting/solvent reservoir or chamber. For HPLC applications, the tubing consists of polytetrafluoroethylene having a diameter of between about 0.062 and 0.125 inches, and with a wall thickness of between about 1 and 3 mils. It has been found that this pre-selected tubing provides enhanced results in functioning as a controlled check valve in the HPLC applications. One end of this tubing is thermoformed in a flat configuration in order for the tubing to function as a check valve in the system.

In addition to performing the function of a check valve, the body of the main valve in which the flexible tubing is installed is provided with a second bore adapted to receive a pressure control member such as a syringe or the like. The bore is further provided with a hand-operated valve which controls the on/off communication between the syringe and the bubble collecting/solvent reservoir. The syringe is utilized to modify and/or control the pressure within the reservoir by significantly reducing the pressure to a level significantly less than atmospheric to achieve flow of captured gas bubbles and solvent into the syringe or out to the pump inlet. The bubble collecting/solvent reservoir may conveniently be an elongated bottle, with the upper portion of the bottle providing a head chamber in which the gas forming the bubbles may be captured for removal prior to entering the system pump. By controlling the position of the hand-operated valve, a syringe may be utilized to both remove the bubble-forming gas, and while the same syringe may be utilized to pressurize the chamber in order to properly prime the HPLC system pump.

Therefore, it is a primary object of the present invention to provide an improved valve arrangement for achieving solvent priming in HPLC applications with a means to capture bubbles or entrained atmosphere.

It is a further object of the present invention to provide an improved check valve means free of lubricants for use in solvent primer means for use in HPLC applications.

Other and further objects of the present invention will become apparent to those skilled in the art upon a study of the following specification, appended claims, and accompanying drawing.

DESCRIPTION OF THE PREFERRED EMBODIMENT

Figure 1:
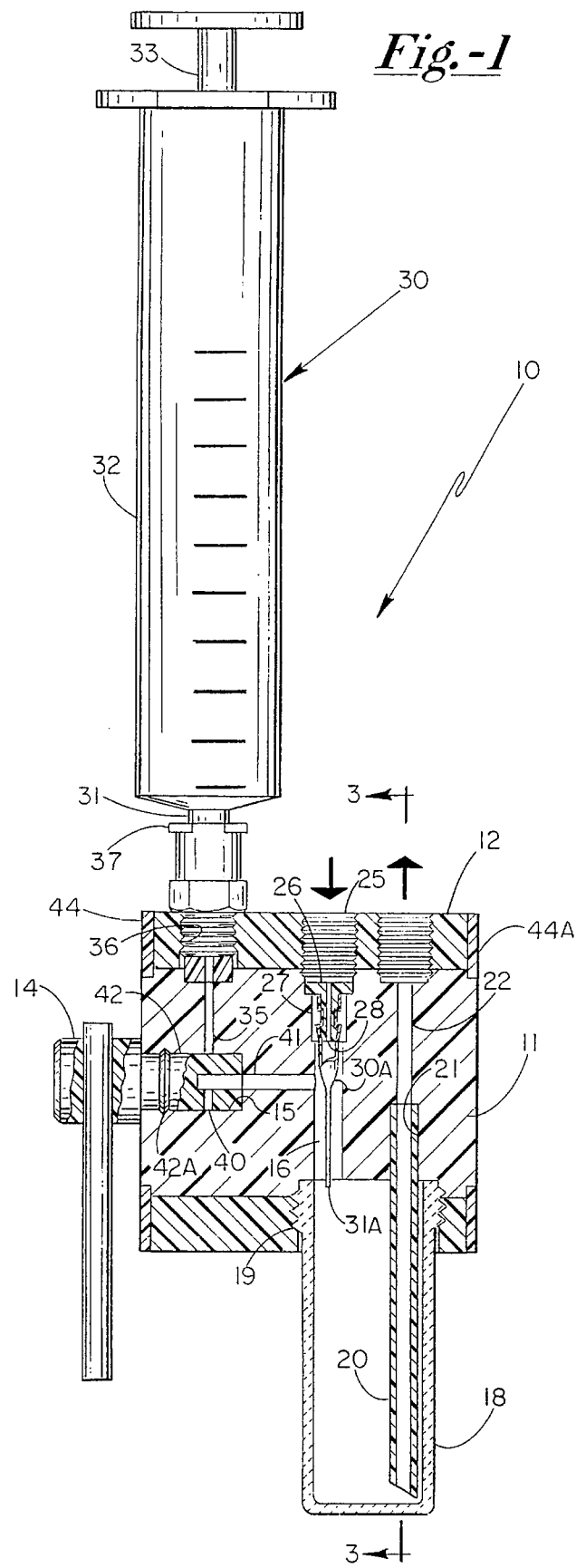
FIG. 1 is a side elevational view, partially in section, illustrating the interior of the valve assembly of the present invention taken generally along a vertical plane through the valve diameter, and also illustrating the check valve and the bubble collecting/solvent reservoir along with a syringe in coupled relationship to the valve.
Figure 2:
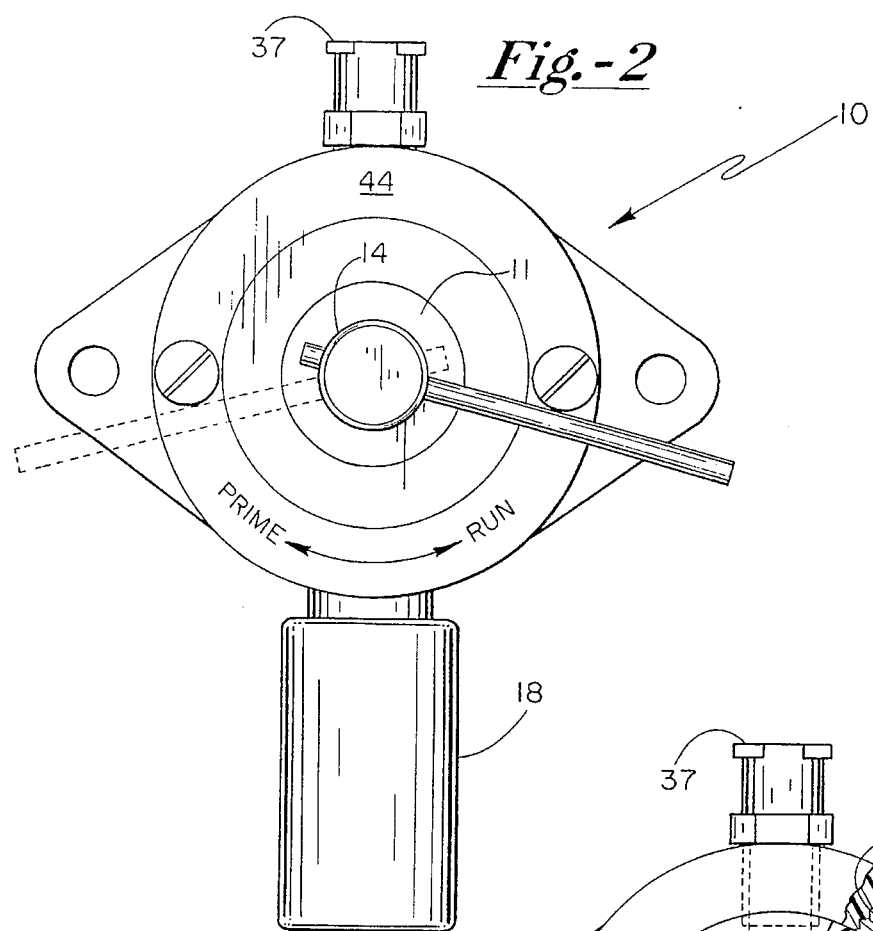
FIG. 2 is a front elevational view of the valve with syringe removed and illustrating the main rotary control valve, and illustrating the valve in its "run" position, and further illustrating, in phantom, the valve in its "prime" position.

In accordance with the preferred embodiment of the present invention, the solvent primer/debubbler valve means generally designated 10 includes a cylindrical core member 11 which is arranged concentrically with outer sleeve member 12. Control valve assembly 14 is positioned within bore 15 formed in core 11, and is arranged in communication with control bore 16 which is a throughbore extending diametrically through cylindrical core member 11 and cylindrical sleeve 12. Bubble collecting/solvent reservoir 18 is threadably engaged within the assembly through counterbore 19 formed in sleeve member 12 and extending partially into core member 11. Solvent pick-up line or tube 20 extends from reservoir 18 into core member 11 through bore 21 formed therein and out through bore 22.

With continued attention being directed to FIG. 1, it will be observed that syringe member generally designated 30 is in operative contact with coupling 37, at its necked-down segment 31. Syringe 30 comprises tubular body 32 along with plunger 33 as is conventional in devices of this type. Syringe 30 is utilized to withdraw trapped gases from the bubble collecting/solvent reservoir 18, by evacuation (withdrawing plunger 33), and alternatively is used to provide for the introduction of positive solvent pressure into the system to prime the main system pump. Normally, gas bubbles migrate to the top of the solvent whenever the syringe plunger is withdrawn.

Figure 3:
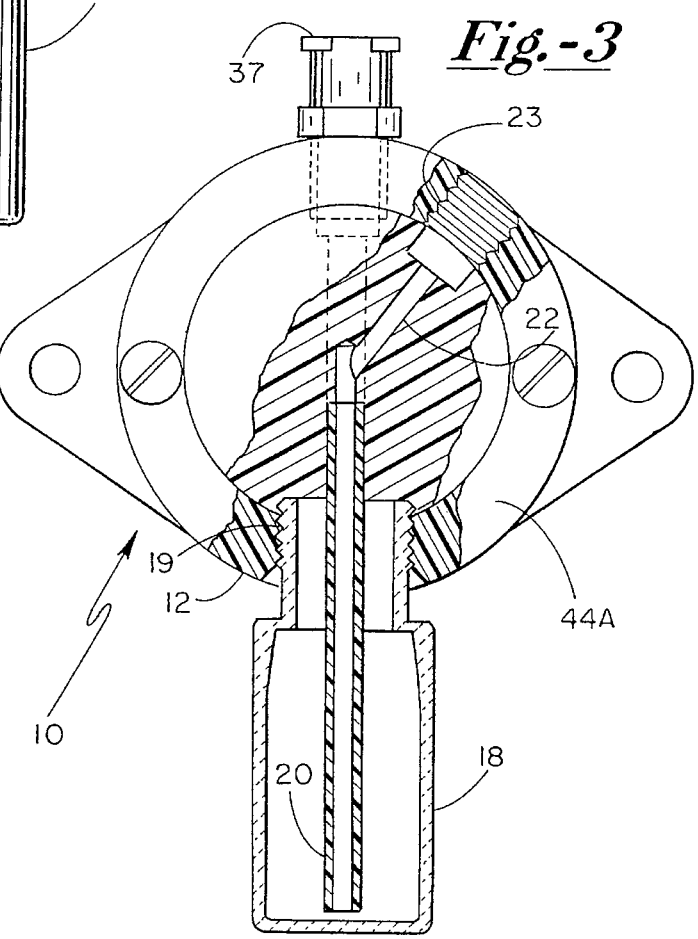
FIG. 3 is an end elevational view shown partially cut away and in section of the valve body illustrated in FIGS. 1 and 2.
Figure 4:
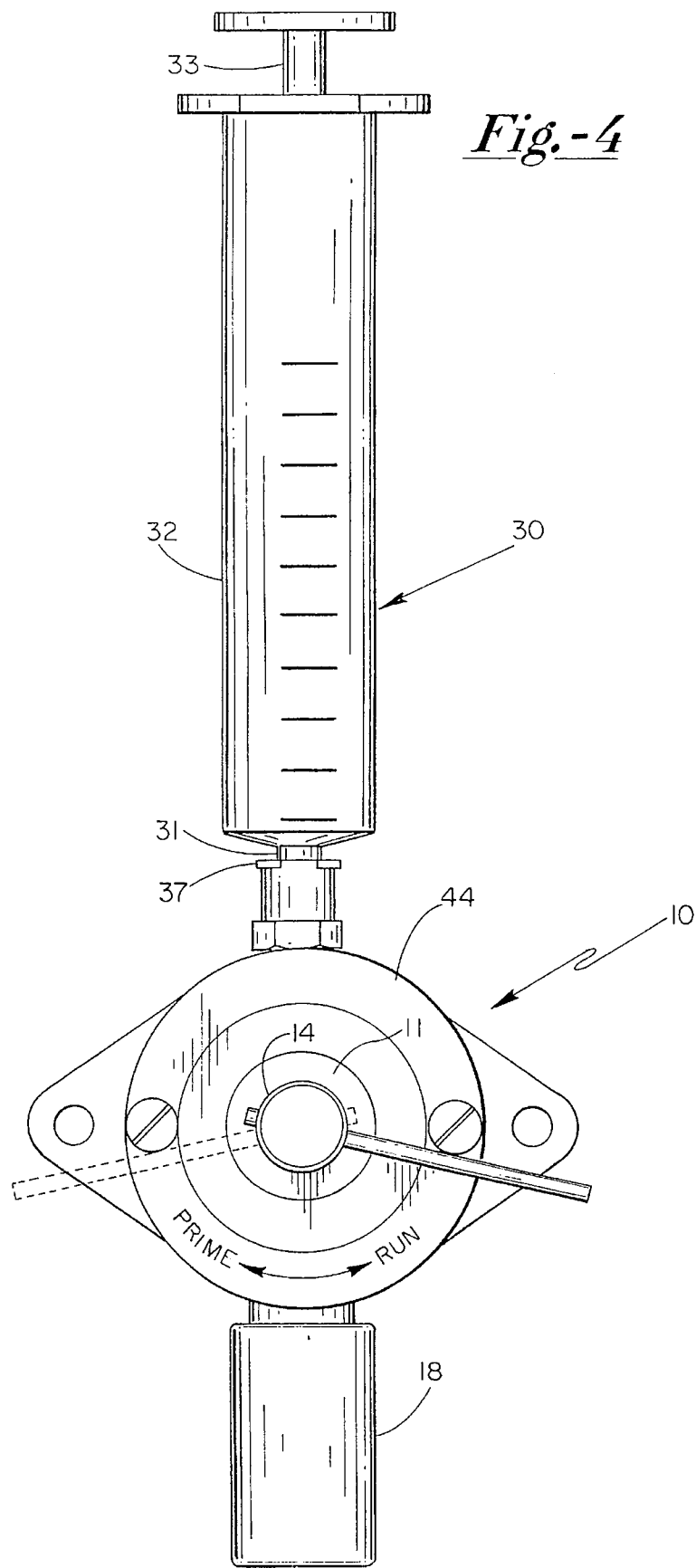
FIG. 4 is a front elevational view, similar to FIG. 2, with the hand valve being held in its "run" position, but illustrating the syringe in contact with the system as illustrated in FIG. 1.

With attention now being directed to FIGS. 1 and 3, it will be observed that the outlet from reservoir 18 proceeds along and through the bore of pick-up line 20 and thence outwardly through discharge bore 22. Bore 22 terminates in a counterbore as at 23 for receiving tubing and/or conduits for ultimately delivering debubbled solvent from reservoir 18 into the HPLC main pump and system.

As shown in FIG. 1, bore 16 is formed in body 11, and it is seen that bore 16 is provided with a counterbore zone as at 25, and is provided with a barbed core member 26 with its flange being held in position within counterbore 25 and with the main body and outer shell 27 of core member 26 having a barbed zone thereon and being disposed tightly within bore 16. The barbed outer shell portion 27 of core member 26 is arranged coaxially with the inner core for retainably and sealingly coupling the length of polytetrafluoroethylene tubing 30A in the annular ring area surrounding core member 26. Tubing member 30A is configured to have an outer diameter less than the inner diameter of bore 16, and also having a wall thickness of between 1 and 3 mils. This ultra thin-walled tubing fabricated from polytetrafluoroethylene, and thermoformed flat at 31, is capable of withstanding pressures generated by hand force on syringe 32, and because of its physical properties, tolerates the assembly constraints as set forth in FIG. 1.

In this arrangement, tubing member 30A is normally exposed to the low pressure side of the main pump, typically at pressures below about 25 psi. This tubing is thermoformed as at 31A to form a flat portion or "duck bill" capable of withstanding reverse pressures in the range of up to about 100 psi. The "duck bill" configuration provides an appropriate check valve to prevent back-flow of solvent, while at the same time permitting inflow or ingress of solvent with low flow restriction from the main solvent supply vessel as will be discussed hereinbelow in connection with the arrangement shown in FIG. 5.

With attention again being directed to FIG. 1 and valve 14, this valve is designed to control the operation of the system through bore 35 and coupling receiving counterbore 36. Coupling 37 is designed to provide pressure control to the system through valve 14 and its internal bores 40 and 41. Rotation of cylindrical valve 14 will cause rotation of valve core member 42 and permit flow, when properly oriented, through bores 35, 40 and 41, and thereby into communication with the head space of the bubble collecting/solvent reservoir 18. A ring seal is formed by expanding a segment of cylindrical valve 14, as at 42A, with this expanded or seal portion shown in somewhat exaggerated configuration in FIG. 1. The expanded portion 42A provides an interference fit within bore 15, thereby sealing valve 14. Fitting or coupling 37 communicates with bore 35, and is designed to accommodate syringes, lines or tubing for transfer of fluids and gases through rotating valve 14 via bores 40 and 41 to and from bubble collecting/solvent reservoir 18. Accordingly, with pressure (approximately 100 psia) being created or encountered in bubble collecting/solvent reservoir 18 through a pressure source, typically syringe/plunger 30/33, coupled to fitting 37, flat portion 31A of tubing 30A collapses and further presses the flat tubing to the disposition illustrated so as to provide a check valve capable of withstanding exposure to typical HPLC solvents. Tubing 30A may also serve as an inlet valve as well as a check valve preventing back-flow with inwardly directed flow of solvent from the main solvent supply vessel 45 being available through tubing-check valve 30A–31A and into bubble collecting/solvent reservoir 18.

Figure 5:
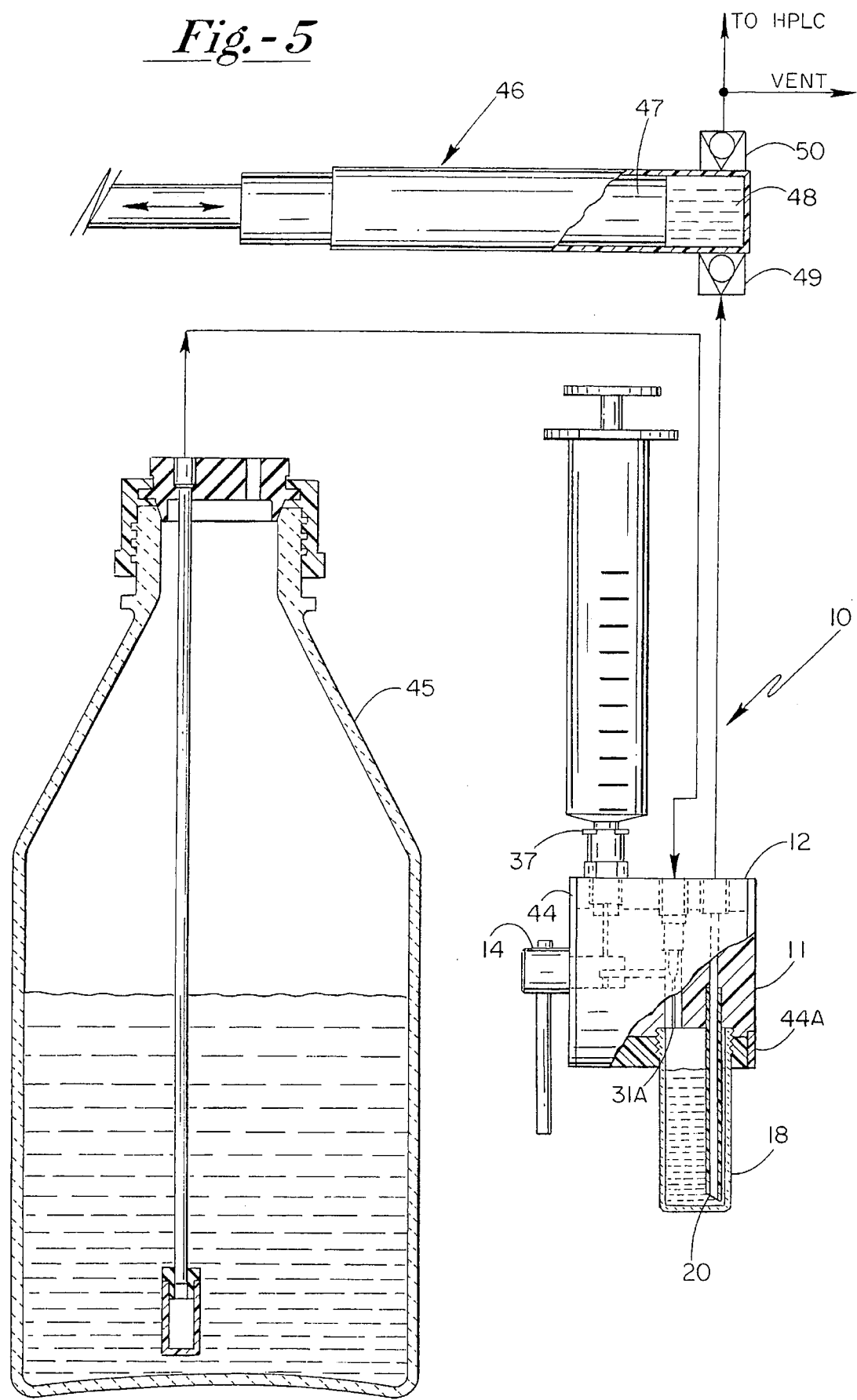
FIG. 5 is a schematic diagram showing an HPLC system, with the valve of the present invention being interposed between a main solvent supply vessel and the system pump.

In a typical application (referring to FIG. 5), a syringe may be utilized to remove gas and solvent from the head zone of the bubble collecting/solvent reservoir 18 through fitting 37. Fitting 37 also serves to pressurize the system and to prime the pump through fluid communication between bubble collecting/solvent reservoir 18 and the system pump 46. System pump 46 is preferably a positive displacement pump employing a reciprocating plunger 47 in communication with chamber 48, with chamber 48 being provided with an inlet check valve as at 49 and an outlet check valve as at 50. As indicated in FIG. 5, the outlet from pump 46 is provided with a vent to atmosphere, as is typical.

TYPICAL APPLICATION CYCLE

1. In a typical application cycle, and by way of example, a 10 mL Luer-Lok syringe is coupled to the port 37. The prime/run valve 14 is moved to the "prime" position in order to establish a communication between the syringe and vial 18. The prime/plunge valve on the HPLC pump, if present, is then opened.

2. Thereafter, syringe plunger 33 is withdrawn (retracted) to evacuate trapped gas retained in the solvent within the vial 18 along with that solvent which flows in through the check valve. The operator holds the syringe plunger in retracted or withdrawn disposition until the syringe is partially filled with solvent and the evacuated trapped gas bubble or bubbles ascend in the syringe to the volume below the plunger, and with internal pressures equalizing such that the plunger does not have the tendency to move back into the syringe barrel.

By way of example, the syringe ideally will have a volume that is approximately three times that of vial 18 (10 cc syringe/3 cc vial), typically providing enough syringe volumetric capacity to withdraw an ample amount of solvent into the syringe for purposes of priming.

3. The operator will then apply a gentle insertion force to the syringe plunger, causing flow out the outlet bore 22, reverse biasing the check valve in order to prevent back-flow into the main solvent reservoir, and causing flow into the HPLC pump inlet check valve. The syringe plunger is inserted until it appears the captured gas may re-enter the system or until the pump is satisfactorily primed.

4. Steps 2 and 3 above may be repeated if the volumetric capacity of the syringe is not sufficiently large to remove captured gas and provide enough solvent to prime the pump. Alternatively, valve 14 may be returned to the "run" position and the operator may disconnect the syringe, invert it, expel the gas, and reconnect the syringe and continue after returning valve 14 to the "prime" position.

5. After satisfactorily priming (typically, solvent flow out the pump vent port is bubble-free), valve 14 is rotated back to the "run" position, closing off communication of the syringe to the flow path through the check valve-vial-solvent pickup line or tube 20.

6. In a typical operation, the syringe is disconnected after priming, inverted, with the gas evacuated from the system being expelled by pushing the plunger inwardly and with the syringe thereafter being reconnected.

MATERIALS OF CONSTRUCTION

With respect to materials of construction, as has been indicated, core member 11 is fabricated from virgin polytetrafluoroethylene, with sleeve member 12 being fabricated from polypropylene or UHMW polyethylene. Abutment or retainer plates 44 and 44A are utilized to help retain and stabilize the assembly in proper orientation and disposition. Cylindrical valve 14 is preferably fabricated from a polyethylether ketone such as "Peek" or a fluorinated material such as, for example, "Kel F". "Kel F" is a trademark of Minnesota Mining and Manufacturing Company of St. Paul, Minn. for the designation of polymers of chlorotrifluoroethylene, with these materials having a hardness which exceeds that of polytetrafluoroethylene. Structures corresponding to the solvent primer valve 10, with the exception of the preferred materials of construction and without the presence of tubing 30A and its associated components are commercially available.

Flanged sleeve 26 is also fabricated from a chlorotrifluoroethylene polymer available under the trademark "Kel F" from Minnesota Mining and Manufacturing Company of St. Paul, Minn. Sleeve 27 and tube 30A are typically fabricated from polytetrafluoroethylene tubing.

For a core member having an outer diameter of up to about 3 inches, this material, fabricated from polytetrafluoroethylene, will be press-fit into a polypropylene shell or sleeve member (shown at 12) having a reduced inner diameter to provide for an interference fit of approximately 0.040 inches. This achieves a tight, effective reliable seal between core member 11 and sleeve member 12.

It will be appreciated that the present description is for illustrative purposes only and the arrangement may be modified without departing from the spirit and scope of the present invention.

What is claimed is:

1. Solvent debubbling/priming means for use in high pressure liquid chromatographic applications and including valving means adapted for releasable and sealed attachment to a bubble collecting HPLC solvent reservoir, the valving means comprising a valve body with bores formed therein for controlled access and communication between said bubble collecting/solvent reservoir and the exterior of said valve, said debubbling priming means being characterized in that:

(a) said valve body consists essentially of an inner core and an outer sleeve arranged concentrically with said core;

(b) said inner core and outer sleeve combination having a plurality of bores formed therein providing communication between said bubble collecting/solvent reservoir and the exterior of said valve and including a plurality of means disposed in cooperative relationship with said bores for controlling flow of fluids to and from said reservoir;

(c) first of said fluid flow control means including a length of flexible tubing disposed within a first of said plurality of bores and with said tubing being in communication with said reservoir and with the outer diameter of said length of tubing being less than the inner diameter of said first bore, said tubing being further characterized in that:

(1) said tubing consists of polytetrafluoroethylene having a diameter of between about 0.062 inches and 0.125 inches and with a wall thickness of between about 1 mils and 3 mils, and having the distal end thereof formed flat by pressure and/or heat to provide a check valve permitting fluid flow in one direction therethrough to a zone of substantially equal or lower pressures.

2. The solvent debubbling/priming means as defined in claim 1 being particularly characterized in that said core member is inserted into said sleeve member under force-fit for forming a seal in the annular contact zone therebetween.

3. The solvent debubbling/priming means as defined in claim 2 wherein the outer diameter of said core member exceeds the inner diameter of said sleeve member by an amount equal to approximately 4% of the diameter of said core member.

4. The solvent debubbling/priming means as defined in claim 3 being particularly characterized in that said core member is fabricated from a material having a hardness less than that of said sleeve member.

5. The solvent debubbling/priming means as defined in claim 4 being particularly characterized in that said core member is fabricated of virgin polytetrafluoroethylene.

6. The solvent debubbling/priming means as defined in claim 5 being particularly characterized in that said sleeve member is fabricated of polypropylene.

7. The solvent debubbling/priming means as defined in claim 6 wherein the outer diameter of said core member is between about 1 inch and 3 inches, and the outer diameter of said core exceeds the inner diameter of said sleeve member by about 4% of the inner diameter of the sleeve.

8. The solvent debubbling/priming means as defined in claim 1 being particularly characterized in that said valving means includes a cylindrical valve core member being mounted and received within a bore formed in said core member and adapted for axial rotation therewithin.

9. The solvent debubbling/priming means as in claim 8 being particularly characterized in that said cylindrical valve core member is fabricated from polymeric chlorotrifluoroethylene.

\* \* \* \* \*